United States Patent [19]

Schmolka

[11] 4,089,814

[45] May 16, 1978

[54] ROLL-ON PERFUME COMPOSITION

[75] Inventor: Irving R. Schmolka, Grosse Ile, Mich.

[73] Assignee: BASF Wyandotte Corporation, Wyandotte, Mich.

[21] Appl. No.: 477,832

[22] Filed: Jun. 10, 1974

[51] Int. Cl.$^2$ .............................. A61K 7/46; C11B 9/00
[52] U.S. Cl. ........................................ 252/522; 424/78
[58] Field of Search ........................... 252/522; 424/78

[56] References Cited

U.S. PATENT DOCUMENTS

| | | | |
|---|---|---|---|
| 3,303,046 | 2/1967 | Chebiniak et al. | 252/522 X |
| 3,708,435 | 1/1973 | Starkman | 252/522 X |
| 3,740,421 | 6/1973 | Schmolka | 424/65 |

OTHER PUBLICATIONS

Cosmetic Formulary, 1965, pp. 7 and 31.

*Primary Examiner*—Dale R. Ore
*Attorney, Agent, or Firm*—Joseph D. Michaels; Bernhard R. Swick; Robert E. Dunn

[57] ABSTRACT

A roll-on perfume composition comprising based on 100 parts by weight of total composition:
(a) from 5 parts to 15 parts of an essential oil,
(b) from 25 parts to 40 parts of an alcohol,
(c) from 20 parts to 40 parts of certain polyoxyethlene polyoxypropylene block copolymers, and
(d) from 5 parts to 50 parts of water.

The resulting compositions are viscous, clear and stable perfumes.

5 Claims, No Drawings

ROLL-ON PERFUME COMPOSITION

BACKGROUND OF THE INVENTION

1. Field Of The Invention

The present invention relates to roll-on perfume compositions. More particularly, the invention relates to certain polyoxyethylene polyoxypropylene block copolymers in the preparation of roll-on perfume compositions.

2. Prior Art

The preparation of roll-on perfume compositions has presented many problems to those skilled in the art. To be an effective roll-on perfume, the composition must be viscous, clear and stable. Moreover, the composition must not contain harmful or irritable skin ingredients. Also, since most perfume oils are water-insoluble, an alcohol or other solvent must be incorporated into the composition in order to obtain homogeneous compositions and also to assist in the volatility of the composition. However, the presence of the alcohol or solvent often results in excessive drying of the skin. Accordingly, there is a need in the art to minimize the presence of the alcohol or solvent in perfume compositions and it is to this end that the present invention is directed.

SUMMARY OF THE INVENTION

The present invention relates to clear, viscous, stable roll-on perfume compositions having a significantly reduced alcoholic content. The compositions of the invention are prepared employing certain polyoxyethylene polyoxypropylene block copolymers. These block copolymers serve four functions, namely: providing thickening to the system, solubilizing the water-insoluble essential oils, reducing the alcohol content of the compositions, and providing lubricity to the composition.

DESCRIPTION OF THE PREFERRED EMBODIMENTS

The roll-on perfume compositions of the present invention comprise based on 100 parts by weight of total composition:
(a) from 5 parts to 15 parts of an essential oil,
(b) from 25 parts to 40 parts of an alcohol,
(c) from 20 parts to 40 parts of a polyoxyethylene polyoxypropylene block copolymer represented by the formula:

$$HO(C_2H_4O)_b(C_3H_6O)_a(C_2H_4O)_bH$$

wherein $a$ is an integer such that the hydrophobe represented by $(C_3H_6O)$ has a molecular weight of from 3250 to 4000 and $b$ is an integer such that the hydrophile portion represented by $(C_2H_4O)$ constitutes from about 50 to 90, and most preferably from 70 to 90, weight percent of the copolymer, and
(d) from 5 parts to 50 parts of water.

One ingredient of the compositions of the subject invention is an essential oil. This is the ingredient which provides the scent to the perfume compositions. There are numerous essential oils sometimes known simply as perfumes, both natural and synthetic, which may be employed in the invention. Almost all essential oils are mixtures of various ingredients. Reference is made to the two-volume treatise *Perfumes, Cosmetics and Soaps*, 1936, D. Van Nostrand Company, Inc., and *The Givaudan Index*, Specifications of Synthetics and Isolates for Perfumery, 2nd Edition, 1961, Givaudan-Delawanna, Inc., for a description of various essential oils. All the essential oils there described may be employed in the subject invention. The particular essential oil employed in the formulation of the compositions of the subject invention is not critical to the invention.

Another ingredient of the compositions of the subject invention is an alcohol. The preferred alcohols are the lower alkanols particularly ethanol, propanol, isopropanol, t-butanol, sec-butanol and n-butanol. Other alcohols which may be employed include propylene glycol, sorbitol, glycerol, dipropylene glycol, pentaerythritol and trimethylolpropane.

Still another ingredient of the compositions of the subject invention are certain polyoxyethylene polyoxypropylene block copolymers. The polyoxyethylene polyoxypropylene block copolymers which may be employed in the present invention may be represented by the formula:

$$HO(C_2H_4O)_b(C_3H_6O)_a(C_2H_4O)_bH \tag{I}$$

wherein $a$ is an integer such that the hydrophobe represented by $(C_3H_6O)$ has a molecular weight of from 3250 to 4000 and $b$ is an integer such that the hydrophile portion represented by $(C_2H_4O)$ constitutes from about 50 to 90, and most preferably from 70 to 90, weight percent of the copolymer. The average total theoretical molecular weight of the copolymers of use in the invention ranges from 6550 to 40,000.

The hydrophobe of the polyoxyethylene polyoxypropylene block copolymers of formula (I), above, is prepared by adding propylene oxide to the two hydroxyl groups of a propylene glycol nucleus. By adding ethylene oxide to the hydrophobe, it is possible to place polyoxyethylene hydrophilic groups on both ends of the molecule. These hydrophilic polyoxyethylene groups may be controlled to constitute anywhere from 50% to 90% of the final molecule. A more detailed explanation of the preparation of these block copolymers may be found in U.S. Pat. No. 2,674,619.

Illustrative block copolymers of formula (I), above, which may be employed in the preparation of the compositions of the present invention are presented in Table I.

Table I

| Copolymer | Mol. Wt. of Hydrophobe (average) | Wt. % of Hydrophile (average) | Approx. Total Mol. Wt. of Copolymer |
|---|---|---|---|
| A | 3250 | 50 | 6,550 |
| B | 3250 | 60 | 8,125 |
| C | 3250 | 80 | 16,250 |
| D | 4000 | 60 | 10,000 |
| E | 4000 | 70 | 13,500 |
| F | 4000 | 80 | 20,000 |
| G | 4000 | 90 | 40,000 |

The compositions of the subject invention are prepared by adding a block copolymer to a water-alcohol solution at a temperature of from about 5° C. to 25° C. and thereafter adding the essential oil thereto. If the temperature of the solution is below room temperature, the resulting solution is allowed to warm to room temperature whereby the viscous, clear solutions of the invention are obtained.

The following examples illustrate the nature of the invention. All parts are by weight unless otherwise indicated.

EXAMPLE I

A roll-on perfume composition was prepared from the following ingredients:

| Parts | |
|---|---|
| 20 | Copolymer E |
| 38 | Ethanol |
| 10 | Essential Oil |
| 32 | Water |

Copolymer E is a 13,500 molecular weight block copolymer of formula (I) having a hydrophobe average molecular weight of 4,000 and a hydrophile constituting 70% by weight of ethylene oxide based on the total weight of the copolymer.

The composition was prepared by adding Copolymer E to the water and alcohol maintained at a temperature of from 5°–10° C. Stirring continued until a homogeneous solution was obtained at which time the essential oil was added and the solution was allowed to warm to room temperature. A viscous, clear composition resulted. The essential oil employed was a peppermint oil. The principal constituents are menthol, menthone, menthyl acetate and menthyl iso-valerate.

EXAMPLE II

Following the procedure of Example I, the following perfume compositions were prepared:

| (A) | Ingredients | Parts |
|---|---|---|
| | Copolymer E | 28 |
| | Ethanol | 28 |
| | Essential Oil B | 10 |
| | Water | 34 |
| (B) | Ingredients | Parts |
| | Copolymer E | 21 |
| | Ethanol | 33 |
| | Essential Oil C | 10 |
| | Water | 36 |
| (C) | Ingredients | Parts |
| | Copolymer B | 33 |
| | Isopropanol | 26 |
| | Essential Oil B | 10 |
| | Water | 31 |
| (D) | Ingredients | Parts |
| | Copolymer F | 25 |
| | t-Butanol | 35 |
| | Essential Oil D | 5 |
| | Water | 35 |
| (E) | Ingredients | Parts |
| | Copolymer C | 25 |
| | Isopropanol | 35 |
| | Essential Oil C | 10 |
| | Water | 30 |

All compositions were viscous, clear compositions which may be employed as roll-on perfume compositions. In the above compositions, the essential oils employed are as follows:

Essential Oil B — Floral composition containing Jasmin, Neroli, Sandalwood, Patchouly, Vetivert, and Rose oils.

Essential Oil C — Chypre oil containing Oakmoss, Rose, Sandalwood, Jasmin, Ylang and Vetivert oil.

Essential Oil D — Rose oil.

The copolymers employed in the above formulations are as described in Table I, above.

The embodiments of the invention in which an exclusive property or privilege is claimed are defined as follows:

1. A roll-on perfume composition comprising based on 100 parts by weight of total composition:
   (a) from 5 parts to 15 parts of an essential perfume oil,
   (b) from 25 parts to 40 parts of an alcohol selected from the group consisting of ethanol, propanol, isopropanol, t-butanol, sec-butanol, and n-butanol,
   (c) from 20 parts to 40 parts of a polyoxyethylene polyoxypropylene block copolymer having a molecular weight of from 6550 to 40,000 represented by the formula:

$$HO(C_2H_4O)_b(C_3H_6O)_a(C_2H_4O)_bH$$

wherein $a$ is an integer such that the hydrophobe represented by $(C_3H_6O)$ has a molecular weight of from 3250 to 4000 and $b$ is an integer such that the hydrophile represented by $(C_2H_4O)$ constitutes from about 50 to 90 weight percent of the copolymer, and
   (d) from 5 parts to 50 parts of water.

2. The composition of claim 1 wherein the alcohol is ethanol.

3. The composition of claim 1 wherein the hydrophobe represented by $(C_3H_6O)$ has a molecular weight of 4000.

4. The composition of claim 1 wherein the hydrophile represented by $(C_2H_4O)$ constitutes from 70 to 90 weight percent of the copolymer.

5. The composition of claim 1 wherein the hydrophobe represented by $(C_3H_6O)$ has a molecular weight of 4000 and the hydrophile represented by $(C_2H_4O)$ constitutes from 70 to 90 weight percent of the copolymer.

* * * * *